United States Patent
Kandori et al.

(10) Patent No.: US 9,055,893 B2
(45) Date of Patent: Jun. 16, 2015

(54) DEGREE OF HARDNESS MEASUREMENT SYSTEM AND DEGREE OF HARDNESS MEASUREMENT METHOD

(75) Inventors: Akihiko Kandori, Tokyo (JP); Kuniomi Ogata, Tokorozawa (JP); Ryuzo Kawabata, Higashiyamato (JP); Yuko Sano, Kokubunji (JP); Takako Mizoguchi, Sayama (JP)

(73) Assignee: Hitachi, Ltd., Tokyo (JP)

( * ) Notice: Subject to any disclaimer, the term of this patent is extended or adjusted under 35 U.S.C. 154(b) by 242 days.

(21) Appl. No.: 13/559,149

(22) Filed: Jul. 26, 2012

(65) Prior Publication Data

US 2013/0085417 A1 Apr. 4, 2013

(30) Foreign Application Priority Data

Sep. 30, 2011 (JP) ................. 2011-217321

(51) Int. Cl.
- *A61B 5/117* (2006.01)
- *A61B 5/103* (2006.01)
- *A61B 5/00* (2006.01)
- *A61B 5/02* (2006.01)

(52) U.S. Cl.
CPC ............. *A61B 5/103* (2013.01); *A61B 5/0053* (2013.01); *A61B 5/02007* (2013.01); *A61B 5/442* (2013.01); *A61B 2562/0219* (2013.01); *G01N 2203/00* (2013.01); *G01N 2203/0075* (2013.01); *G01N 2203/0076* (2013.01)

(58) Field of Classification Search
USPC .................................. 600/587; 601/41; 73/78
See application file for complete search history.

(56) References Cited

FOREIGN PATENT DOCUMENTS

JP 10-211172 A 8/1998

*Primary Examiner* — Brian Szmal
(74) *Attorney, Agent, or Firm* — Miles & Stockbridge P.C.

(57) ABSTRACT

For measuring hardness of an object, a measurement apparatus is pushed against the object and a degree of hardness calculation system calculates hardness based on information from the measurement apparatus. The measurement apparatus includes an acceleration sensor which outputs first information of acceleration of a contact area of the measurement apparatus, and a second sensor, such as a magnetic sensor or a pressure sensor, which outputs second information based on pressure applied to the contact area. The degree of hardness calculation system generates a second-derivative waveform by twice differentiating a waveform based on the output of the second sensor, compares the second-derivative waveform and the information of acceleration from the acceleration sensor, and calculates hardness of the object based on the comparison result.

5 Claims, 12 Drawing Sheets

FOR CASE OF SPRING CONSTANT = 0.935 kgf/mm (a) CALCULATED DISPLACEMENT BASED ON MAGNETIC SENSOR (b) DISPLACEMENT SENSOR OUTPUT

DEGREE OF HARDNESS MEASUREMENT SYSTEM AND DEGREE OF HARDNESS MEASUREMENT METHOD

CLAIM OF PRIORITY

The present application claims priority from Japanese patent application JP 2011-217321 filed on Sep. 30, 2011, the content of which is hereby incorporated by reference into this application.

The present invention relates to a technology of measuring hardness of a subject, for example human body.

BACKGROUND OF THE INVENTION

It is very useful to measure the hardness of a subject. For example, in the case that the subject is human body, it is possible to know the hardness of muscle and internal organs and to determine a degree of progress of arterial sclerosis, and to develop a plan of treatment by measuring a degree of hardness at a predefined position of the body.

For example, Japanese Unexamined Patent Application No. Hei 10-211172 (Patent Document 1) describes that an acceleration sensor and a pressure sensor are pushed against human body, and measuring hardness of the subject (elastic coefficient) based on pressure information and acceleration information which is integrated two times.

As a commonly-used hardness measuring apparatus, there is a durometer. By using the durometer, the hardness of the subject is measured based on the depth of a dent made by a needle which is pushed against the body.

SUMMARY OF THE INVENTION

The patent document 1 discloses that the acceleration is integrated two times. However, when the acceleration is integrated two, times, the error becomes large and the measurement accuracy of hardness is lower.

On the other hand, the durometer is suited to the subject such as rubber and plastic for which the area surrounding where needle is pushing does not sink in so much. But the durometer is not well suited for a subject like the human body for which the surrounding area and the area that the needle is pushing sink in together.

According to the present invention, the degree of hardness of the subject is measured with a high degree of accuracy regardless of how much the subject sinks in when the subject is pushed.

DETAILED DESCRIPTION OF THE PREFERRED EMBODIMENTS

Hereinafter, embodiments of the degree of hardness measurement system according to the invention are described in detail with reference to the drawings.

Figure 1:
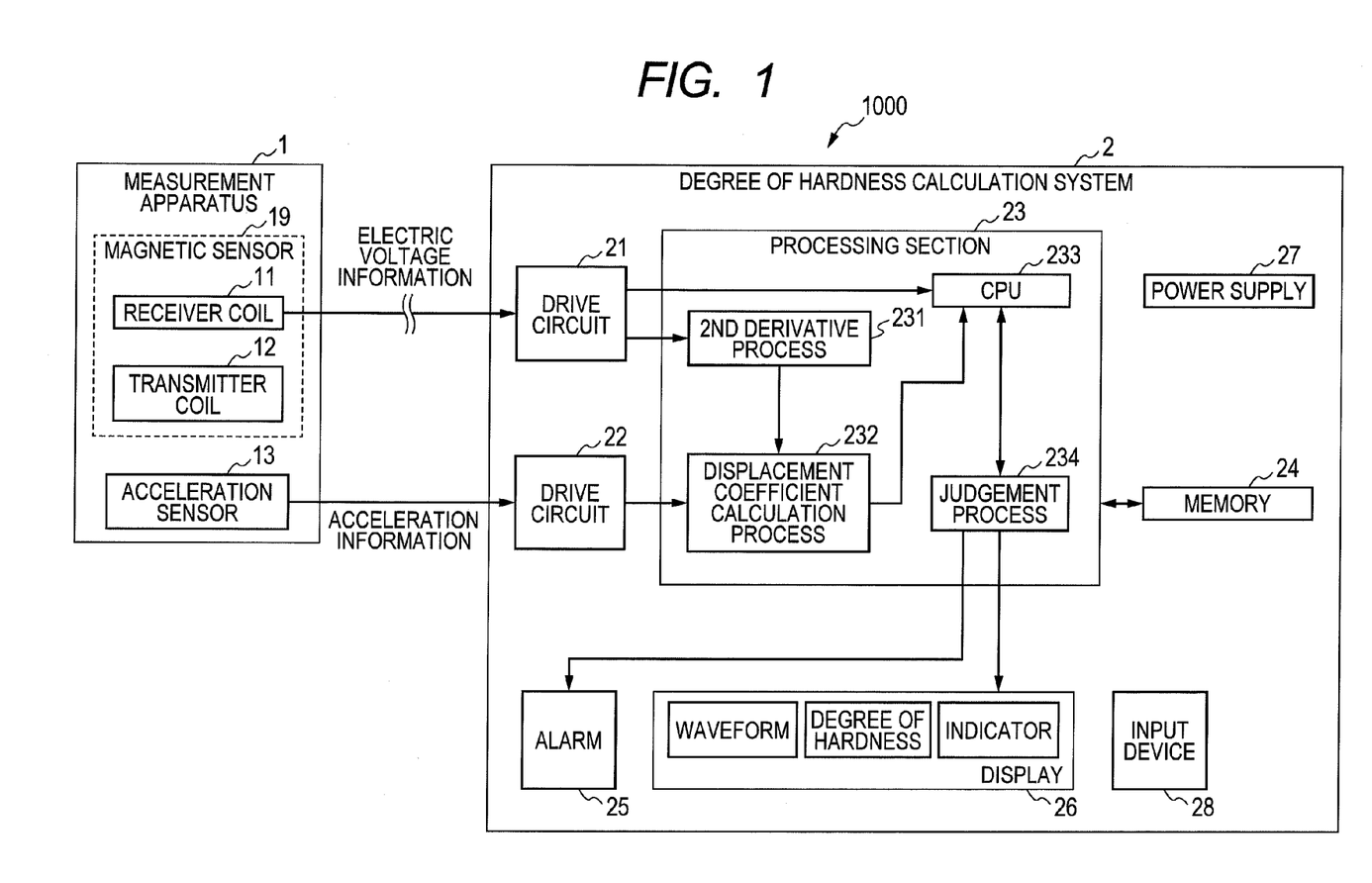
FIG. 1 is a view illustrating a block diagram of one example of a degree of hardness measurement system.
Figure 2:
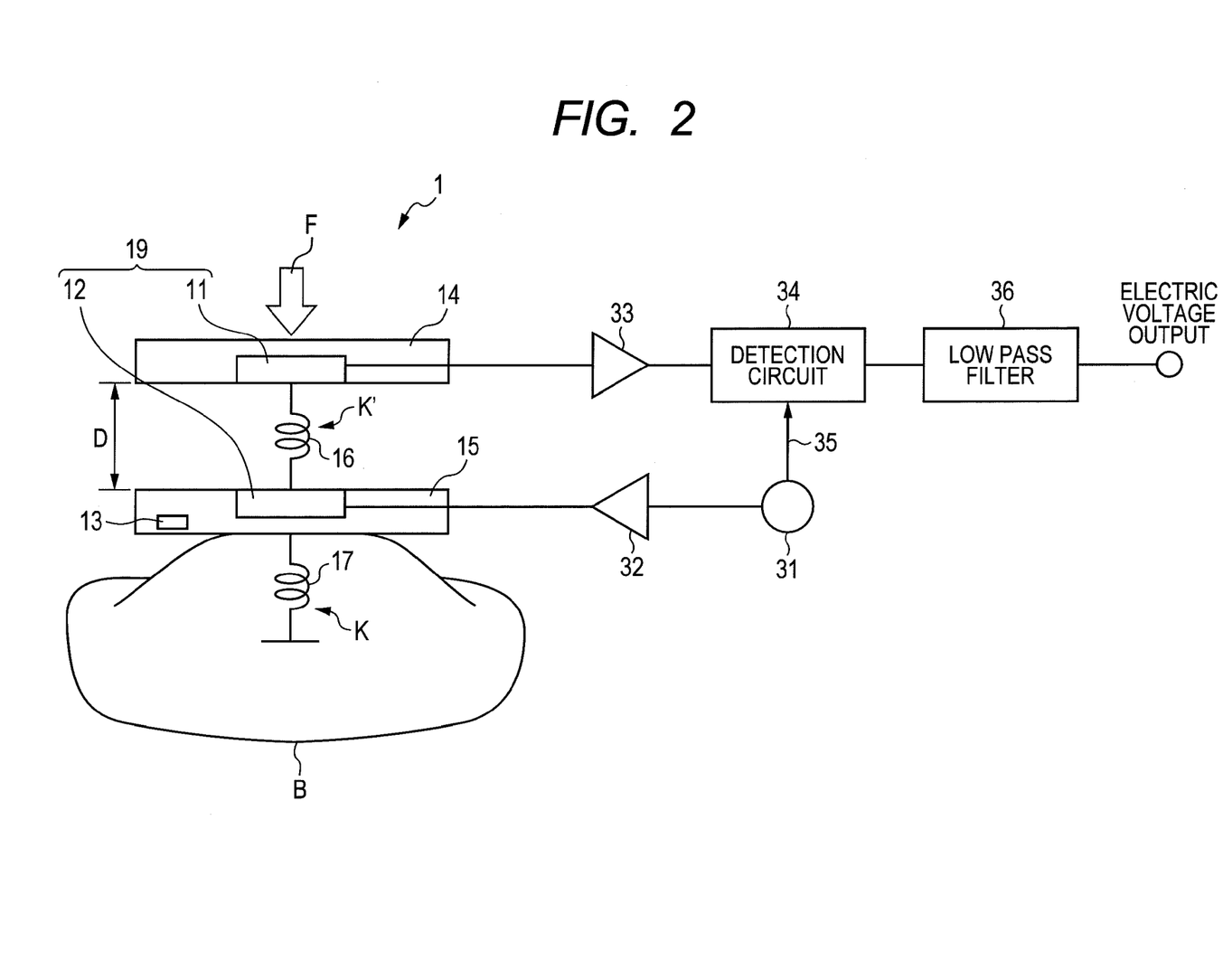
FIG. 2 is a view illustrating the operating principle of a measurement apparatus.

FIG. 1 shows a degree of hardness measurement system 1000 which comprises a measurement apparatus 1 and a degree of hardness calculation system 2. With reference to FIG. 1 and FIG. 2, the composition and operating principle of the measurement apparatus 1 are now explained. The measurement apparatus 1 includes a housing 14 which has a receiver coil 11 (magnetic field detecting means), a contact area 15 which has transmitter coil 12 (magnetic field generating means) an acceleration sensor 13, and at least one spring 16 (elastic body). Here the receiver coil 11 and transmitter coil 12 constitute a magnetic sensor 19.

The contact area 15 is pushed against a portion B of a human body (as one example, B is breast region) which is a measurement subject so that the body yields under pressure of the contact area 15 applied by the operator of the measurement apparatus 1. The housing 14 and the contact area 15 are rigid. An acceleration sensor 13 detects acceleration information of a direction in which the body is pushed. Although the body portion B has both spring behavior and damper behavior, the spring behavior is dominant. So the body portion B is assumed as a spring 17 that has a spring constant K. Calculating K of the spring 17 is a feature of this embodiment.

The magnetic sensor 19 outputs information as electric voltage based on the pressure applied to body portion B by the measurement apparatus 1. Therefore, the receiver coil 11 and the transmitter coil 12 are located facing each other. A spring 16, having a known spring constant K' is disposed between the housing 14 and the contact area 15. The spring 16 is chosen so that K'>K. Otherwise, the housing 14 could contact the contact area 15 when press force F is applied to the housing 14 (see FIG. 2) so that the magnetic sensor 19 would not work. As one example of the measurement apparatus 1, a distance D between the housing 14 and the contact area 15 is about 2 mm, and the amount of compression of the spring 16 is 0.5 mm.

Next, behaviors of the magnetic sensor 19 and associated components are explained. First, an alternating current oscillator 31 produces AC voltage which has specific frequency (one example, 20 kHz). The AC voltage is converted to an AC current which has specific frequency by amplifier 32, and the AC current which was converted flows to the transmitter coil 12. A Magnetic field produced by AC current flowing to the transmitter coil 12 causes an induced electromotive force in the receiver coil 11.

AC current generated in the receiver coil 11 by the induced electromotive force is amplified by preamplifier 33, and the amplified signal is inputted to a detection circuit 34. The detection circuit 34 detects the amplified signal of the specific frequency produced by the AC oscillator 31. Therefore, the output of the AC oscillator 31 is inputted to a reference signal input terminal of the detection circuit 34 as a reference signal 35. In another embodiment, a full-wave rectification circuit can be used without using detection circuit 34. Electric voltage output from the detection circuit 34 (or rectification circuit) is passed through a low pass filter 36 and input to a processing section 23 of a degree of hardness calculation system 2 (FIG. 1). The arrangement indicated by reference numbers 31-36 in FIG. 2 constitutes a drive circuit 21 for the magnetic sensor 19. The drive circuit is incorporated in the degree of hardness calculation system 2 in the embodiment of FIG. 1.

Figure 4:
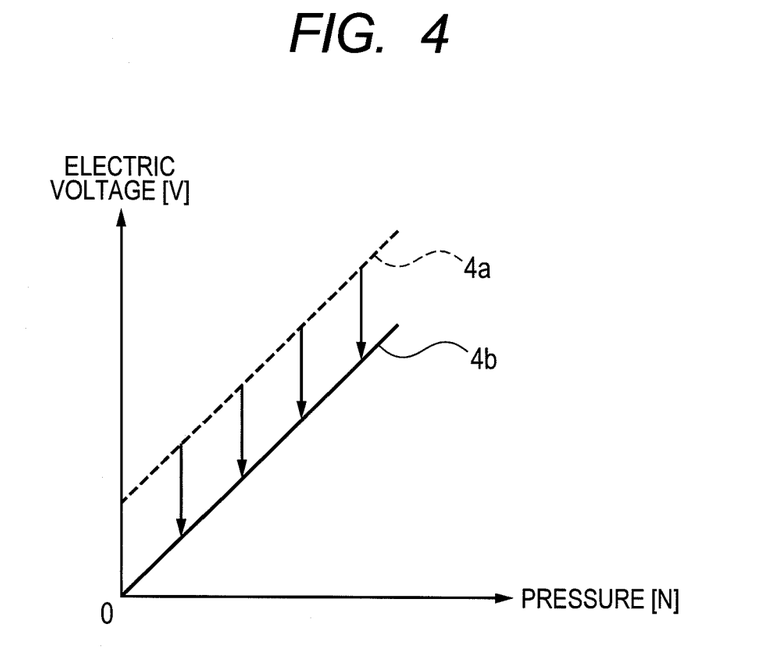
FIG. 4 is a view illustrating one example of relation of electric voltage and pressure.

A relationship between pressure (force F) applied to the housing 14 and the electric voltage which is input to the drive circuit 21 is shown at 4a (dashed line) in FIG. 4. The reason why a line 4a is a straight line is that spring constant K' of spring 16 is big and that the amount of compression of spring 16 is small. The relationship between the pressure and the voltage can be corrected by correcting line 4a to line 4b, such that when pressure is 0 voltage is also 0. This correction is made by a processing section 23 which is explained below. A displacement coefficient, which describes the ratio between the voltage information that the magnetic sensor outputs and pressure which is applied to the body portion B, is expressed as Cmp[N/mV], an electric voltage/pressure displacement coefficient. Cmp is preliminarily calculated from experiment.

Secondly, the degree of hardness calculation system is explained (FIG. 1). The degree of hardness calculation system is a computer system and includes drive circuits 21, 22, processing section 23, memory 24, alarm 25, display 26, power supply 27, and input device 28.

Drive circuit 21 outputs electric voltage information that the drive circuit 21 received from receiver coil 11 through low pass filter 36 (FIG. 2) to processing section 23. Drive circuit 22 outputs acceleration information received from acceleration sensor 13 to processing section 23.

Figure 5:
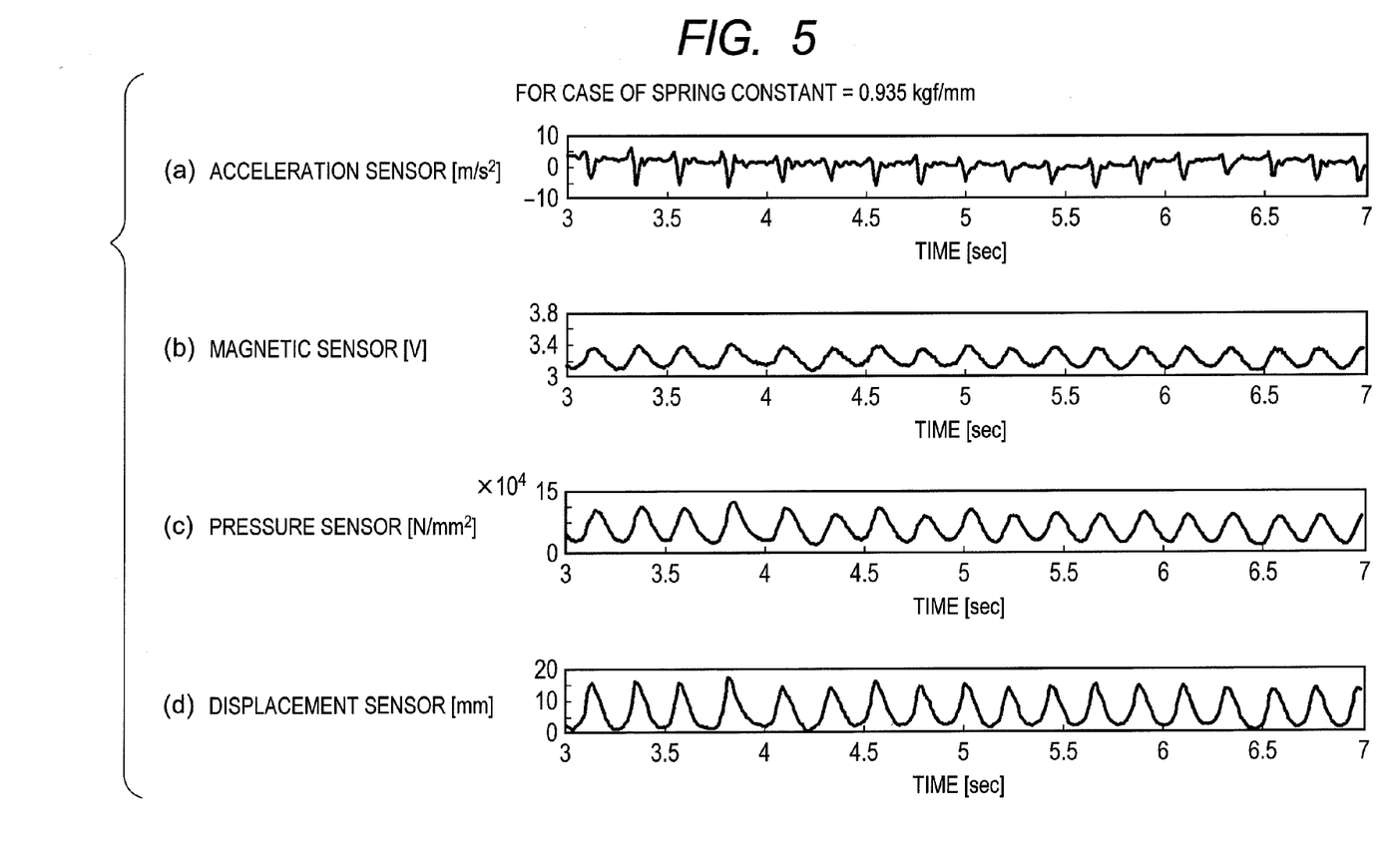
FIG. 5 is a view illustrating one example of outputs of acceleration sensor, a magnetic sensor, a pressure sensor and a displacement sensor for a case of spring constant=0.935 kgf/mm.
Figure 6:
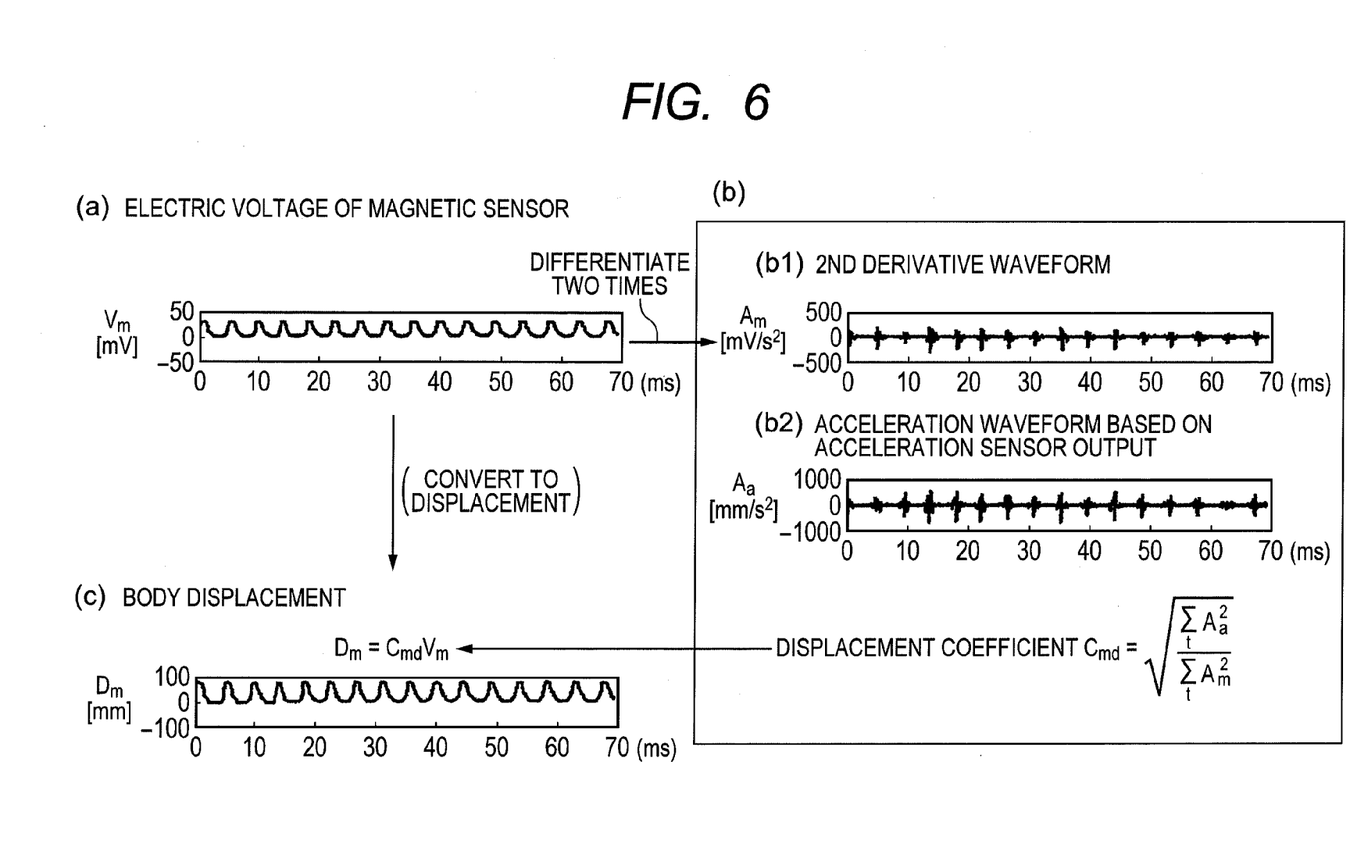
FIG. 6 is a view illustrating an output of electric voltage of a magnetic sensor ($a$), a 2nd derivative waveform ($b1$), an acceleration waveform based on acceleration sensor output ($b2$), and a body displacement waveform ($c$)
Figure 7:
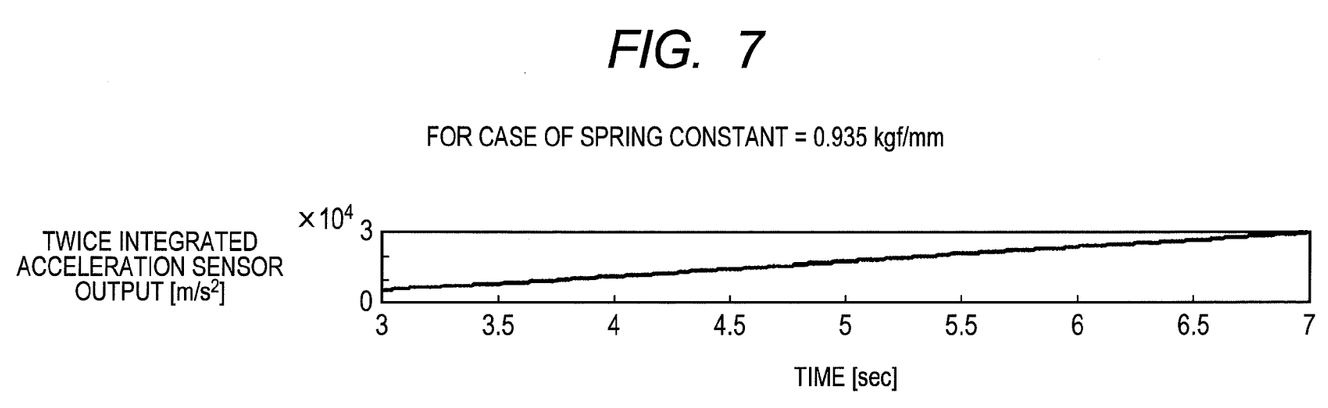
FIG. 7 is a view illustrating a twice integrated acceleration sensor output for case of the spring constant=0.935 kgf/mm.
Figure 8:
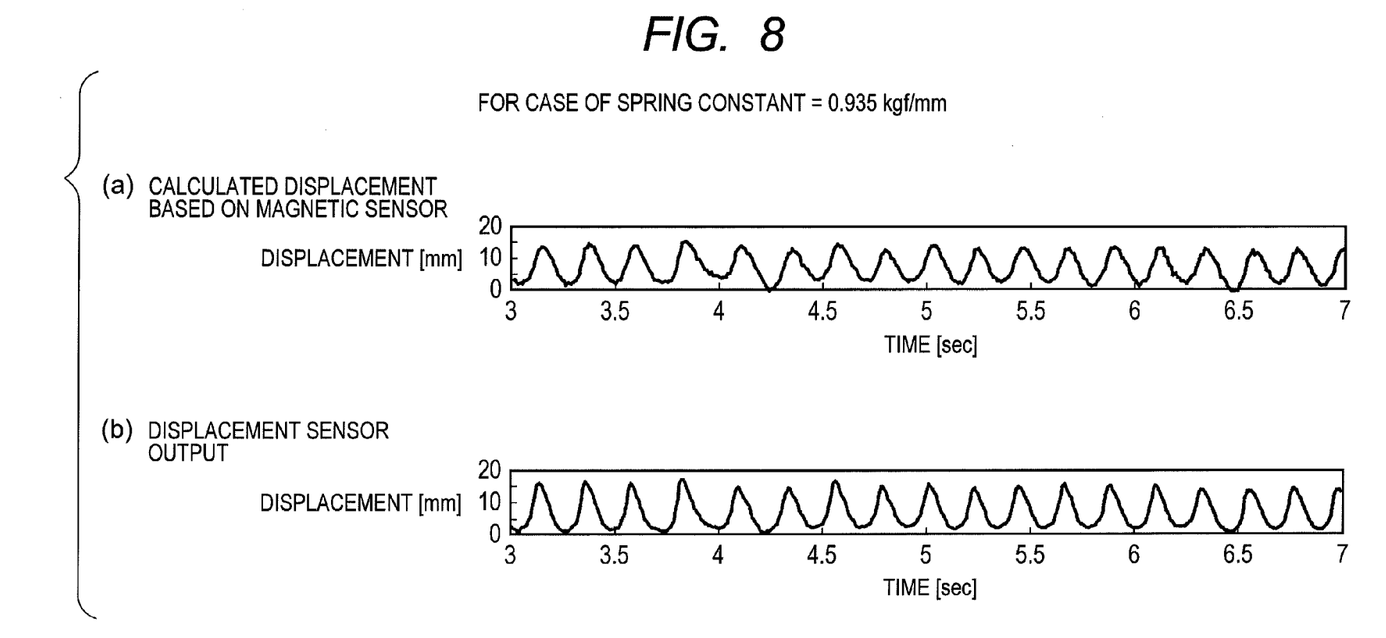
FIG. 8 is a view illustrating a calculated displacement, based on magnetic sensor ($a$), and displacement sensor output ($b$) for the case of spring constant=0.935 kgf/mm.

Processing section 23 includes 2nd derivative process 231, displacement coefficient calculation process 232, CPU (Central Processing Unit) 233 and judgement process 234. FIG. 5-7 explains their operations.

FIG. 5. shows outputs of an acceleration sensor 13 (a), a magnetic sensor 19 (b), a pressure sensor (c) used as an alternative to a magnetic sensor (a pressure sensor is not drawn in figures), and a displacement sensor (d) measured as a reference (a displacement sensor (d) is not drawn in figures and the out put of the displacement sensor is the real displacement value), when the reference spring constant K' is 0.935 kgf/mm.

An object of this embodiment is to calculate a physical object's spring constant. The physical object is indicated as the spring 17 in FIG. 2. And from the spring constant, the hardness of the physical object is calculated. Therefore, a first step is to get closest information of (d) by using at least one information within the outputs of (a), (b) and (c) in FIG. 5. And a second step is to calculate the spring constant (or calculate hardness) of the physical object (spring 17 in FIG. 2) by using the closest information.

That is to say, information of the acceleration sensor (a) and the magnetic sensor (b) are used to calculate the spring constant (or hardness), without using the displacement sensor (d) such as laser sensor. The reasons why the displacement sensor is not used are that it is difficult to use in some circumstances and that the displacement sensor is expensive. Also, when the acceleration is integrated two times, the error becomes bigger when time passes. See FIG. 7. So this technique is not useful for the present invention.

Comparing the waveform of the magnetic sensor 19 (b) and the displacement sensor (d), it can be seen that the shapes are very similar and frequency is the same, although units of vertical axes are different and amplitudes are different. Therefore, the displacement sensor's approximate waveform output is to be calculated by multiplying waveform output of the magnetic sensor 19 (b) by a displacement coefficient (Cmd [mm/mV]). Cmd is calculated as indicated in FIG. 6 and indicates a ratio between the acceleration waveform and the 2nd derivative waveform. The waveform of a pressure sensor (c) is similar to that of the magnetic sensor 19 (b).

Now the calculation of spring constant (or hardness) of the physical object is explained. When the amount of compression of the spring 17 (FIG. 2) is X and electric voltage output of magnetic sensor 19 is Vm, the following formulae (1), (2) and (3) apply. Based on the law of action and reaction, force F (pressure) reacts to the contact portion 15 and contact area of the body portion B.

$$F = K \times X \qquad \text{formula (1)}$$

$$X = Cmd \times Vm \qquad \text{formula (2)}$$

$$F = Cmp \times Vm \qquad \text{formula (3)}$$

Formula (1) indicates Hooke's Law. Formula (2) indicates that displacement X is calculated by multiplying output electric voltage of magnetic sensor 19 by Cmd. Formula (3) indicates that pressure F is calculated by multiplying electric voltage Vm from magnetic sensor 19 by Cmp.

And the following formula (4) is obtained by substituting formula (2) and formula (3) in formula (1).

$$K = Cmp / Cmd \qquad \text{formula (4)}$$

That is to say, the spring constant K (or hardness) of the physical object is calculated by Cmp divided by Cmd.

Returning to FIG. 1, memory 24 is an information storing means such as ROM (Read Only Memory), HDD (Hard Disk Drive) and so on. Memory 24 stores Cmp which is already calculated from experiment.

Alarm 25 is a sound generating means, for example a speaker. The alarm 25 generates a beep sound when the measurement apparatus 1 starts or finishes measurement. Display 26 is an information displaying means, for example an LCD (Liquid Crystal Display) or a CRT (Cathode Ray Tube) display. Display 26 displays one or more of waveforms, hardness of physical object, and an indicator which visually represents hardness.

Power supply 27 is a power supplying means for the degree of hardness calculation system 2. Input device 28 is an information inputting means for information is inputted by user, for example a keyboard or mouse.

Figure 3:
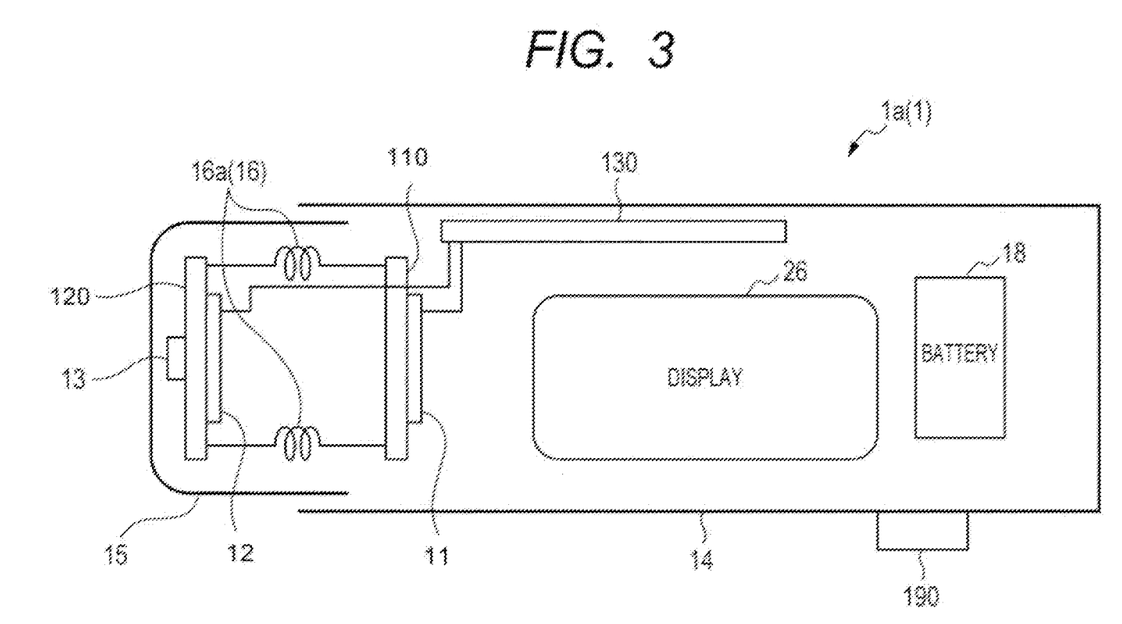
FIG. 3 is a diagrammatic view illustrating one example of measurement apparatus.

Here, one example of measurement apparatus 1 is explained referring to FIG. 3. Points already explained in discussing FIG. 2. are omitted. The measurement apparatus 1a (1) is a pencil shape having housing 14 and contact portion 15.

The housing 14 houses receiver coil 11, coil base 110 equipped with the receiver coil 11, circuit base for mounting the various circuit components and which is connected to the receiver coil 11 and the transmitter coil 12, battery 18, a start button which is operated when measurement is to start and the display 26.

Contact portion 15 houses transmitter coil 12, acceleration sensor 13, coil base 120 equipped with the transmitter coil 12 and the acceleration sensor 13. There is a spring 16a (16) between the coil base 110 and the coil base 120. The number of springs 16a (16) can be one or 2 to 4, or even more as suits a particular application. As a simple model, the spring 16a (16) is one spring and diameter of the spring 16a (16) is same size or bigger than diameters of coil base 110 and receiver coil 11. When there is only one spring, the coil base 110 and the receiver coil 11 can be equipped inside the spring. So the measurement apparatus 1 can be smaller.

When the contact portion 15 is pushed against a physical object, spring 16a (16) is compressed and the receiver coil 11 and transmitter coil 12 come closer together and the magnitude of magnetic field that the receiver coil 11 detects becomes bigger. So the measurement apparatus 1a (1) outputs electric voltage based on the magnitude of pressure applied to the contact portion 15. In addition, the measurement apparatus 1a (1) is pencil shape and very useful because it is small.

Figure 9:
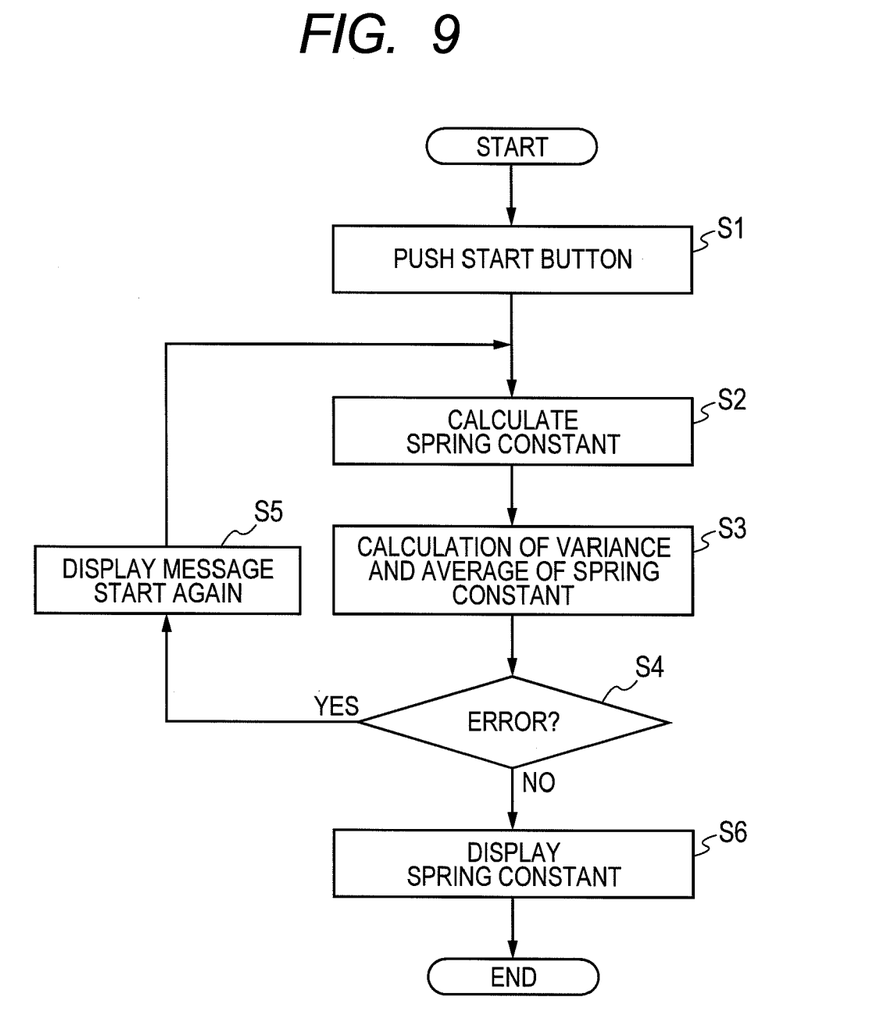
FIG. 9 is a flowchart illustrating a procedure for measurement by the degree of hardness measurement system.

FIG. 9 shows a flowchart and explains the process of degree of hardness calculation system 2. First, the start button 190 is pushed by the operator (Step S1). The contact portion 15 is pushed against the physical object several times by the operator.

Processing section 23 in degree of hardness calculation system 2 calculates the spring constant (or hardness) of the physical object based on the information from the measurement apparatus 1a (1) (Step S2. The detail is explained FIG. 10).

The processing section in degree of hardness calculation system 2 calculates an average amount and a variance of a plurality of spring constants which are calculated in Step S2 (Step S3). Then judgement process 234 judges whether the average and variance are abnormal values or not (Step S4). The judgement is performed by comparing with predetermined thresholds. When the judgement is Yes, Step 5 is next step. The processing section 23 makes the display 26 display an alert and the process goes back to the Step S2. When the judgement is No, Step 6 is next step. For example, when the operator's hand which is holding the measurement apparatus 1 is shaking, detecting accuracy of the acceleration sensor is low, and then the judgement is YES (case of abnormal value).

The processing section 23 makes the display 26 display the spring constant (or hardness), and then the process ends. The display 26 displays the average of the spring constants, for example.

Figure 10:
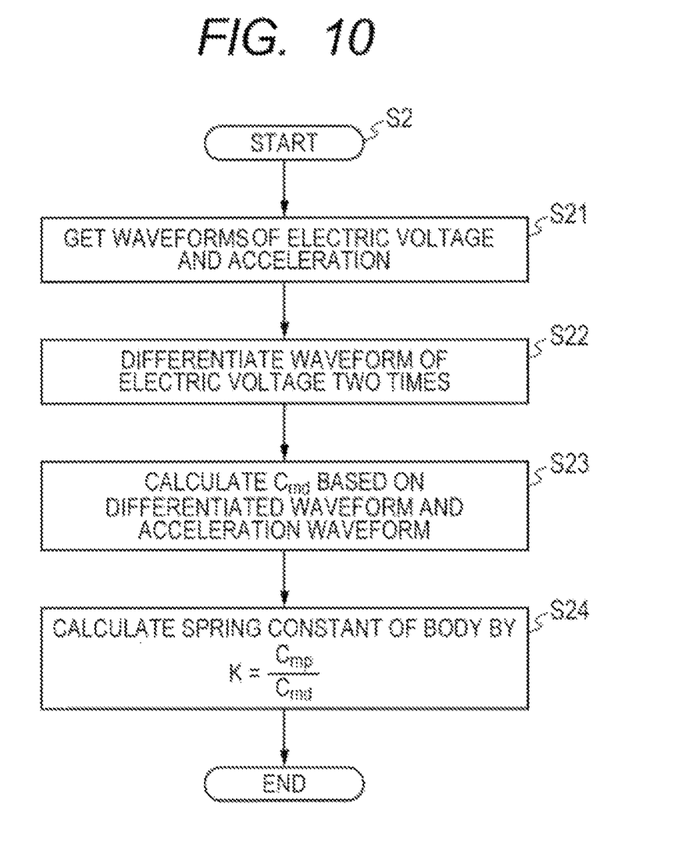
FIG. 10 is a flowchart illustrating a calculation of spring constant by the degree of hardness measurement system.

FIG. 10 explains a process of calculating the spring constant (or hardness) of the physical object by the degree of hardness calculation system 2. The process is Step S2 in FIG. 9. The Step S2 in FIG. 9 is a step of calculating spring constant (or hardness) several times. FIG. 10. explains how to calculate the spring constant (or hardness) each time.

First, processing section 23 gets a waveform of electric voltage based on electric voltage information from magnetic sensor 19, and a waveform of acceleration based on acceleration information from acceleration sensor 13 (Step S21).

2nd derivative process 231 generates twice differentiated waveform of electric voltage by differentiating the waveform of electric voltage two times (Step S22. FIGS. 6 (*a*) and (*b*1)).

Displacement coefficient calculation process 232 compares the differentiated waveform and acceleration waveform (FIG. 6 (*b*2)) and outputs the result of comparison, and CPU 233 calculates Cmd based on the result of comparison (Step 23). For example, Cmd is calculated using the following formula (FIG. 6 (*b*))

formula (5)

$$C_{md} = \sqrt{\frac{\sum_t A_a^2}{\sum_t A_m^2}}$$ 式(5)

Next, CPU 233 calculates spring constant K (or hardness) of the physical subject by dividing Cmp by Cmd (Step 24). Then the process ends.

As just described, degree of hardness measurement system 1000 enables high accuracy calculation of hardness of the physical object regardless how the object sinks in when the object is pushed, by calculating Cmd by comparing the twice differentiated waveform of electric voltage from magnetic sensor 19 and the acceleration waveform from acceleration sensor 13, and calculating spring constant (or hardness) of the physical subject by dividing Cmp which is predetermined by Cmd. Especially this invention achieve higher accuracy compared to the prior art that integrates the output of an acceleration sensor two times. And by using magnetic sensor 19 this invention achieves a measurement apparatus 1 that is small and low cost.

Second Embodiment

Figure 12:
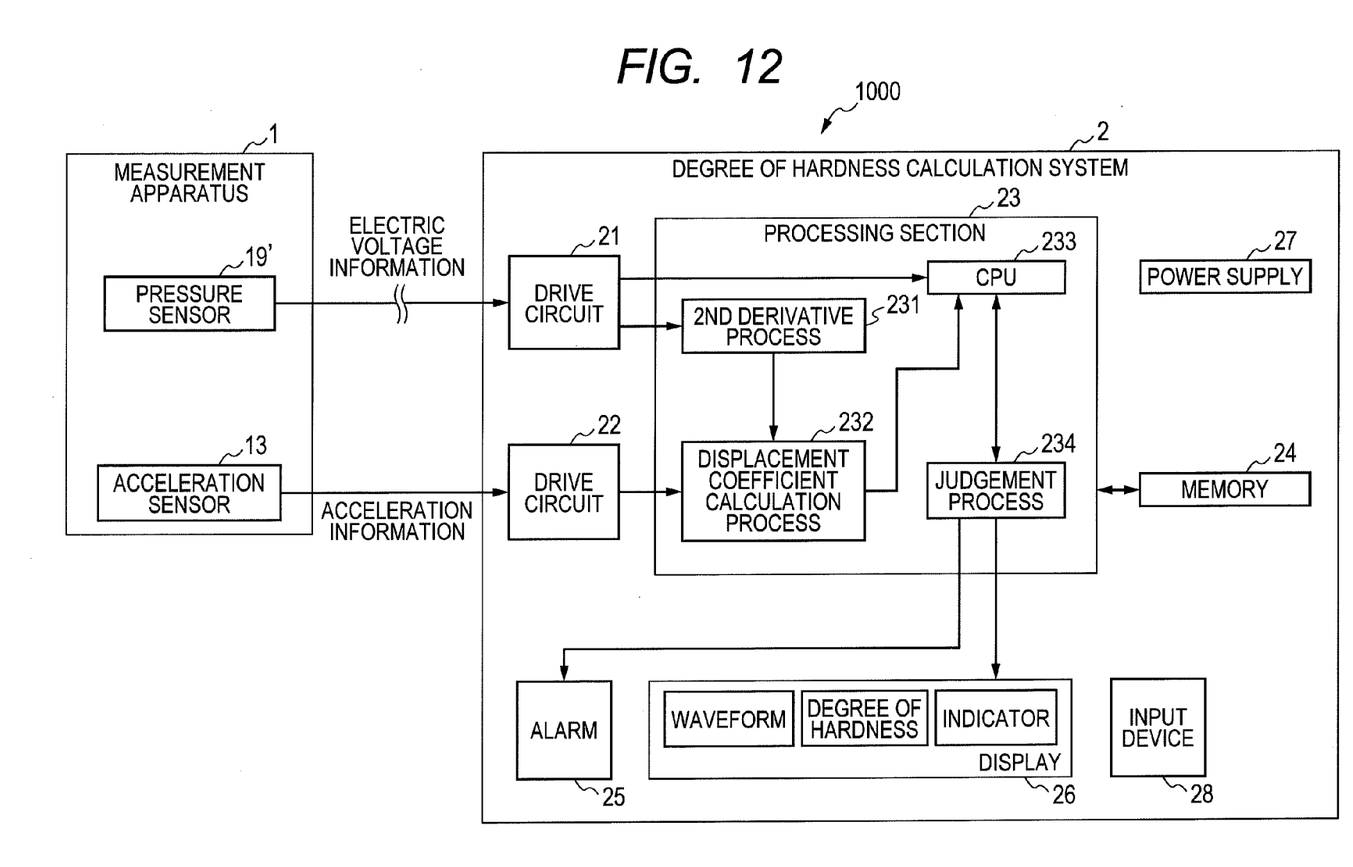
FIG. 12 is a block diagram of a degree of hardness measurement system according to a second embodiment.

In a second embodiment, shown in FIG. 12, a pressure sensor 19' is used instead of magnetic sensor 19 of the first embodiment. The pressure sensor can be a strain gauge, piezoelectric, capacitive, electromagnetic, a tuning fork, piezoelectric semiconductor and so on.

And in the process of Step S22 in FIG. 10, instead of electric voltage, the 2nd derivative process 231 differentiates pressure information two times. In the process of Step S24 in FIG. 10, CPU 233 calculates spring constant by Cmp=1, because pressure is being detected directly and the conversion used for the magnetic sensor thus becomes unnecessary.

Third Embodiment

Figure 11A:
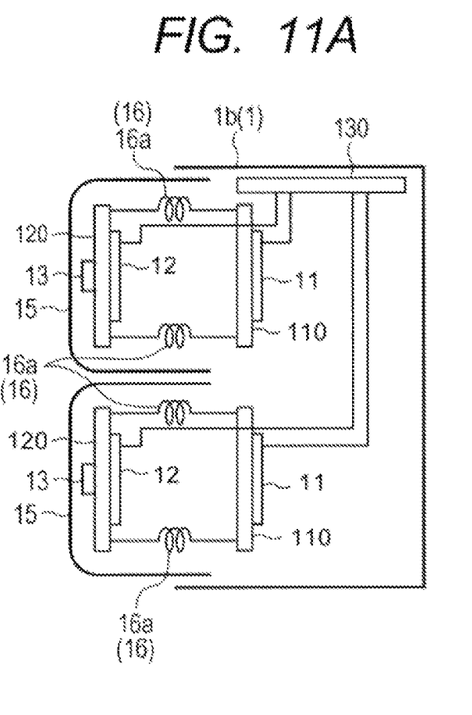
FIG. 11A is a view illustrating one example of a measurement apparatus which provide two contact portions.

The third embodiment is a measurement apparatus 1b(1) which provides more than two contact portions 15. It enables to calculate more than two spring constants at the same time. So it is possible to use average of the spring constants, to calculate a difference between a target area and a region adjacent to the target area, and to use the highest accuracy spring constant.

Fourth Embodiment

Although in the first embodiment, the physical object is exemplified as a breast region B in FIG. 2, other areas are also suitable as the physical object. For example, in the field of obstetrics and gynecology, this invention can be used to measure hardness of the mouth of the uterus of a pregnant female. As one example in this case, the measurement apparatus 1 can be attached to an ultrasound system.

In the field of orthopedic surgery, this invention is used for measuring hardness of muscle. For example, tension or stiffness of muscle can be measured. And in the field of cosmetic medicine, this invention can be used for measuring hardness of skin.

Also in the field of surgery, the measurement apparatus 1 can be attached to an endoscope tip of finger shape to be used for measuring hardness of entrails or the liver.

Figure 11B:
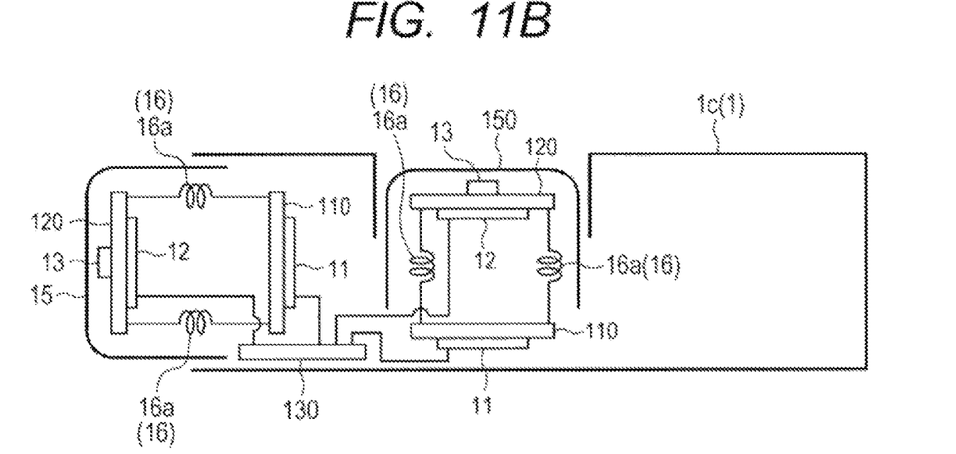
FIG. 11B is a view illustrating an example of a measurement apparatus with provides a second pressure measurement area.

In the field of cardiac internal medicine, this invention is used for measuring hardness of an inside wall of the heart or the degree of progression of arterial sclerosis. In this case, very small coils (receiver coil 11 and transmitter coil 12) and acceleration sensor 13 are used in measurement apparatus 1. For example, as shown in FIG. 11B a second pressure measurement area 150 is provided besides contact portion 15 in measurement apparatus 1c (1). The second pressure measurement area can measure fluid pressure in a blood vessel. Then correct the hardness of a physical object can be measured by contact portion 15 based on the value of the fluid pressure in blood vessel measured by second pressure measurement area 150. The contact portion 15 and the second pressure measurement area 150 are pushed by fluid pressure. So rebound element such as a balloon can be provided to the root of one or both of the contact portion 15 and the second pressure measurement area 150.

Several embodiments of this invention have been described above. But this invention is not limited by the above embodiments. For example, one example of an elastic body in measurement apparatus 1 is spring 16, but rubber or other elastic material is also useful.

Also, at Step S1 in FIG. 9, start button 190 is operated when the process starts. But the process can start when the contact portion 15 is under some pressure without start button 190 being pushed.

To measure physical objects wherein the ranges of hardness are different from each other, several measurement apparatus 1 can be provided with different springs, or the spring 16 of one measurement apparatus can be replaced with other springs of which the spring constants are different. The physical object includes not only human beings, but also other things that need their hardness to be measured.

What is claimed is:

1. A hardness measurement system for measuring hardness of an object, comprising:
   a measurement apparatus disposed to be pushed against the object; and
   a degree of hardness calculation system coupled to said measurement apparatus and operative to calculate hardness based on information from said measurement apparatus;
   wherein said measurement apparatus includes:
   an acceleration sensor operative to output first information of acceleration of a contact area of said measurement apparatus toward said object; and
   a magnetic sensor operative to output second information as electric voltage based on magnitude of pressure applied to said contact area; and
   wherein said degree of hardness calculation system includes:
   a memory operative to store third information of a relationship between said electric voltage from said magnetic sensor and said magnitude of pressure; and
   a processing section configured to generate a 2nd derivative waveform by twice differentiating an electric voltage waveform based on said electric voltage output from said magnetic sensor, to compare said 2nd derivative waveform and said information of acceleration from said acceleration sensor, and
   to calculate hardness of said object based on a result of said comparison and said relationship information stored in said memory.

2. The hardness measurement system according to claim 1, wherein said relationship information is information regarding displacement of said contact area in a direction of pushing.

3. The hardness measurement system according to claim 2, wherein said relationship information includes a first displacement coefficient representing a relationship between voltage and pressure;
   said comparison result is a second displacement coefficient representing a relationship between voltage and displacement;
   and said processing section calculates said hardness by dividing said first displacement coefficient by said second displacement coefficient.

4. The hardness measurement system according to claim 1, wherein said magnetic sensor comprises:
   a transmitter coil; and
   a receiver coil operative to output electric voltage based on magnitude of a magnetic field transmitted by said transmitter coil,
   wherein said receiver coil is connected said transmitter coil by an elastic body, and said receiver coil outputs electric voltage based on magnitude of pressure applied to said contact area of said measurement apparatus toward said object when said measurement apparatus is pushed against said object, said elastic body yields and said transmitter coil and said receiver coil come closer to each other, and the magnitude of the magnetic field that said receiver coil detects is increased.

5. A hardness measurement system for measuring hardness of object, comprising:
   a measurement apparatus disposed to be pushed against the object; and
   a degree of hardness calculation system coupled to said measurement apparatus and operative to calculate hardness based on information from said measurement apparatus;
   wherein said measurement apparatus includes:
   an acceleration sensor operative to output information of acceleration of a contact area of said measurement apparatus toward said object; and
   a pressure sensor operative to output information of pressure applied to said contact area; and
   wherein said degree of hardness calculation system includes:
   a processing section configured to generate a 2nd derivative waveform by twice differentiating a pressure waveform based on said pressure information from said pressure sensor, to compare said 2nd derivative waveform and said information of acceleration from said acceleration sensor, and to calculate hardness of said object based on a result of said comparison.

* * * * *